(12) United States Patent
Shima et al.

(10) Patent No.: US 7,262,849 B2
(45) Date of Patent: Aug. 28, 2007

(54) METHOD OF POLISHING THIN FILM FORMED ON SUBSTRATE

(75) Inventors: Shohei Shima, Tokyo (JP); Akira Fukunaga, Tokyo (JP)

(73) Assignee: Ebara Corporation, Tokyo (JP)

( * ) Notice: Subject to any disclaimer, the term of this patent is extended or adjusted under 35 U.S.C. 154(b) by 114 days.

(21) Appl. No.: 11/128,364

(22) Filed: May 13, 2005

(65) Prior Publication Data

US 2005/0254051 A1 Nov. 17, 2005

(30) Foreign Application Priority Data

May 14, 2004 (JP) ............................. 2004-145535

(51) Int. Cl.
*G01J 4/00* (2006.01)
(52) U.S. Cl. ...................... 356/364; 356/369
(58) Field of Classification Search ................ 356/364, 356/369, 630, 632
See application file for complete search history.

(56) References Cited

U.S. PATENT DOCUMENTS

| | | | |
|---|---|---|---|
| 6,464,563 B1* | 10/2002 | Lensing | 451/6 |
| 6,510,395 B2* | 1/2003 | Stanke | 702/81 |
| 6,690,473 B1* | 2/2004 | Stanke et al. | 356/601 |
| 6,710,889 B2* | 3/2004 | Lee et al. | 356/630 |
| 6,917,433 B2* | 7/2005 | Levy et al. | 356/630 |
| 6,930,771 B2 | 8/2005 | Rosencwaig et al. | |
| 6,939,209 B2 | 9/2005 | Tsuo et al. | |
| 6,946,394 B2* | 9/2005 | Fielden et al. | 438/680 |
| 6,980,300 B1* | 12/2005 | Lensing et al. | 356/601 |
| 2002/0022936 A1* | 2/2002 | Stanke | 702/81 |
| 2005/0254050 A1* | 11/2005 | Fielden et al. | 356/369 |

OTHER PUBLICATIONS

Alessandra Satta et al., "The Removal of Copper Oxides by Ethyl Alcohol Monitored In Situ by Spectroscopic Ellipsometry", Journal of the Electrochemical Society, 150(5) G300-G306 (2003), 0013-4651/2003/150(5)/G300/7, The Electrochemical Society, Inc.
M. R. Baklanov et al., "Characterization of Cu surface cleaning by hydrogen plasma", J. Vac. Sci. Technol. B., vol. 19, No. 4, Jul./Aug. 2001, 1071-1023/2001/19(4)/1/11, American Vacuum Society.

* cited by examiner

*Primary Examiner*—Roy M. Punnoose
(74) *Attorney, Agent, or Firm*—Wenderoth, Lind & Ponack, L.L.P.

(57) ABSTRACT

A method for polishing a thin film formed on a substrate includes planarizing a thin film formed on a reference substrate by a CMP process such that the thin film remains on the reference substrate. After the planarizing, the thin film is cleaned, and then values of $\Delta$ and $\Psi$ with respect to the cleaned thin film are measured by ellipsometry. A physical property of the thin film is determined based on the $\Delta$ and $\Psi$ which have been measured by ellipsometry, and a polishing condition for an other substrate having a thin film to be polished is set based on physical property data which are obtained by the determining of the physical property.

5 Claims, 5 Drawing Sheets

METHOD OF POLISHING THIN FILM FORMED ON SUBSTRATE

BACKGROUND OF THE INVENTION

1. Field of the Invention

The present invention relates to a method of polishing a thin film formed on a substrate, and more particularly to a polishing method which can properly polish a thin film by determining a physical property and a thickness of the thin film utilizing ellipsometry.

2. Description of the Related Art

Ellipsometry is a method of determining the refractive index of a specimen by emitting polarized light to a flat surface of the specimen and measuring a change in the polarization state of reflected light. Ellipsometry is also used for determining a thickness of a thin film formed on a surface of a specimen.

Fabrication processes of an IC chip include a process of forming thin films of several kinds of materials on a substrate (e.g., Si substrate) and a process of removing the thin films using CMP (i.e., chemical mechanical planarization). In a case of a copper thin film, for example, an oxide film such as CuO or $CuO_2$ is likely to be formed on a surface of the copper thin film. Therefore, while performing a CMP process, a pressing force should be properly adjusted when pressing the oxide film against a polishing pad and when pressing a highly pure copper after the oxide film is removed. Accordingly, when performing a CMP process, it is desirable to know the thickness of the oxide film in advance so as to set a proper polishing condition based on the thickness of the oxide film.

Ellipsometry is conducted by emitting linearly polarized light to a thin film, and measuring a phase angle $\Delta$ of elliptically polarized light reflected from the thin film and a tangent $\Psi$ that is given by a magnitude ratio of amplitude of the elliptically polarized light. If an optical constant (i.e., a complex refractive index) of a material forming the thin film is known, the thickness of the thin film can be determined based on the relationship between the optical constant and $\Delta$ and $\Psi$ as measured.

However, with respect to the copper thin film formed on the substrate in an IC chip fabrication process or other process, it has been found that it is not appropriate to determine the film thickness by such ellipsometry using the optical constant of copper which is published in handbooks, documents, and the like. FIG. 1 shows this fact. In FIG. 1, a mark ● shows $\Delta$ and $\Psi$ measured by ellipsometry. In this case, the measurement of $\Delta$ and $\Psi$ is performed after a copper thin film on a substrate has been planarized by CMP to remove an oxide film from the thin film and the thin film has then been cleaned. Marks ○ show time-series data of $\Delta$ and $\Psi$ measured by ellipsometry when oxidization proceeds after the planarization.

On the other hand, marks ♦, ▲, and ■ show $\Delta$ and $\Psi$ calculated using optical constants (i.e., complex refractive indexes) published in handbooks and documents. These optical constants are given with respect to copper having a clean surface with no oxide film thereon. As can be seen from FIG. 1, there is an obvious difference between the values of $\Delta$ and $\Psi$ which are actually measured with respect to the copper film and the oxide film on the substrate and the values of $\Delta$ and $\Psi$ calculated using the optical constants which are commonly known. Specifically, FIG. 1 shows that the thickness of the thin film cannot be accurately determined from the commonly known complex refractive index and the values of $\Delta$ and $\Psi$ measured by ellipsometry.

Japanese laid-open patent publication No. 07-193033 discloses a related art of this technical field.

SUMMARY OF THE INVENTION

The present invention has been made in view of the above drawbacks. An object of the present invention is to accurately determine a thickness of a thin film of copper or other material formed on a substrate using ellipsometry so as to properly polish the thin film on the substrate.

In order to solve the above drawbacks, according to one aspect of the present invention, there is provided a method of polishing a substrate formed on a substrate comprising planarizing a thin film formed on a reference substrate by a CMP process such that the thin film remains on the reference substrate. The planarized thin film is cleaned, and then values of $\Delta$ and $\Psi$ with respect to the cleaned thin film are measured by ellipsometry. A physical property of the thin film is determined based on $\Delta$ and $\Psi$ which have been measured, and a polishing condition for an other substrate having a thin film to be polished is set based on the physical property which has been determined.

In a preferred aspect of the present invention, the thin film of the reference substrate has an oxide film on a surface thereof before the planarizing is performed. During the planarizing, the oxide film is removed so that an exposed surface of the thin film is formed on the reference substrate. During the cleaning, the exposed surface of the thin film is cleaned. In the measuring, $\Delta$ and $\Psi$ with respect to the thin film which has been cleaned are measured by ellipsometry, and $\Delta$ and $\Psi$, with respect to an oxide film which is formed on the thin film after the cleaning, are measured by ellipsometry with predetermined time intervals.

In a preferred aspect of the present invention, the determining a physical property includes determining a thickness of the oxide film based on $\Delta$ and $\Psi$ measured with respect to the oxide film. A thickness of the oxide film on the thin film formed on the other substrate is determined based on thickness data obtained by the determining a thickness.

In a preferred aspect of the present invention, the thickness of the thin film remaining on the reference substrate is set as a reference thickness. Refractive index of the thin film is determined based on the reference thickness and $\Delta$ and $\Psi$ obtained by the measuring of the thin film remaining on the reference substrate. $\Delta$ and $\Psi$ corresponding to thicknesses and refractive indexes, both of which are near the reference thickness and the determined refractive index, are calculated. A relationship between the thicknesses, the refractive indexes, and the calculated $\Delta$ and $\Psi$ is determined. Ellipsometry is performed on the oxide film formed on the thin film of the reference substrate with predetermined time intervals so as to measure $\Delta$ and $\Psi$. Thicknesses corresponding to the measured $\Delta$ and $\Psi$ are determined from the relationship. The thickness of the oxide film on the thin film formed on the other substrate is determined based on data of the determined thicknesses.

In a preferred aspect of the present invention, in a case where film formation processes on the reference substrate and the other substrate are performed simultaneously under the same conditions, the thickness of the oxide film of the other substrate is determined based on the thickness data obtained by the determining of the thickness and a period of time from when the thin film is formed on the other substrate to when the CMP process is performed on the other substrate.

As described above, in the present invention, the thin film, which is actually formed on the substrate, is polished by the CMP process, so that the oxide film is removed. Thereafter, the substrate is cleaned, and ellipsometry is then performed to measure the thickness of the thin film and the oxide film which is formed on the thin film after cleaning. Therefore, the film thickness can be measured very accurately, and hence the CMP processing of the thin film can be performed properly.

DETAILED DESCRIPTION OF THE PREFERRED EMBODIMENT

A polishing method according to an embodiment of the present invention will be described with reference to the drawings. The polishing method of the present invention is performed with a CMP apparatus, i.e., a chemical mechanical planarization apparatus. The CMP apparatus comprises at least one cassette in which a plurality of substrates, each having a film of copper or other material, are accommodated. The substrates are sequentially removed from the cassette and delivered to a turntable (polishing table). Each substrate is pressed against a polishing pad attached to the turntable and is thus polished to have a flat surface. The substrate, which has been planarized, is returned to the cassette via a cleaning station, a drying station, and other equipment.

Figure 3:
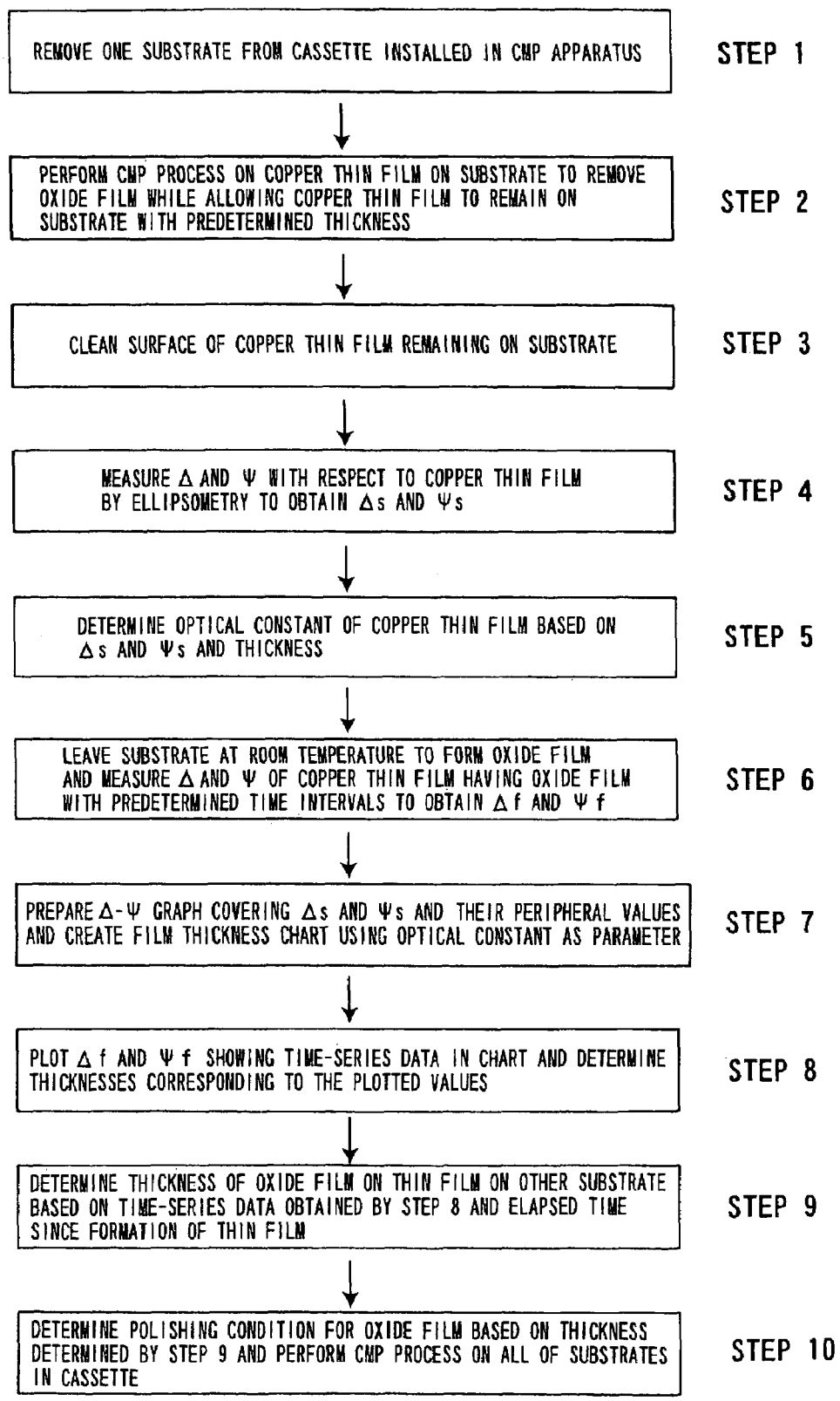
FIG. 3 is a flow chart showing a process of the polishing method according to an embodiment of the present invention.

The polishing method according to the embodiment of the present invention is designed to enable a CMP process, i.e., a chemical mechanical planarization process, to be performed properly. Specifically, this method performs measurement of the thickness of a thin film formed on a substrate using ellipsometry, obtains data on the film, especially data on film thickness determined by the measurement, and performs the CMP process based on the data obtained. The polishing method of the embodiment is performed according to a process illustrated in FIG. 3.

STEP 1 (Sampling Step):

A substrate serving as a reference substrate is removed from the cassette which has been loaded into the CMP apparatus. The substrate has a thin film of copper or other material formed on a surface thereof, and an oxide film has been formed on the surface of the thin film with the passage of time since the formation of the thin film. Although one reference substrate is used in the embodiment, two or more reference substrates may be used.

STEP 2 (Planarization Step):

The removed substrate is planarized with the CMP process to have a flat and smooth surface at the nano level. The CMP process is performed such that the oxide film is removed and the thin film remains on the substrate with a predetermined thickness d (reference thickness). In this case, an eddy current film-thickness sensor or an optical film-thickness sensor is used for measuring the film thickness. Although these sensors can measure the thickness of the copper film, they cannot measure the thickness of the copper oxide film.

STEP 3 (Cleaning Step):

After the CMP process, the thin film is cleaned so that abrasive particles, which are used in the CMP process, are removed and a damaged surface layer is also removed.

Figure 4:
FIG. 4 is a scanning electron micrograph showing a surface of a copper film which has been planarized and cleaned with an inorganic acid solution.
Figure 5:
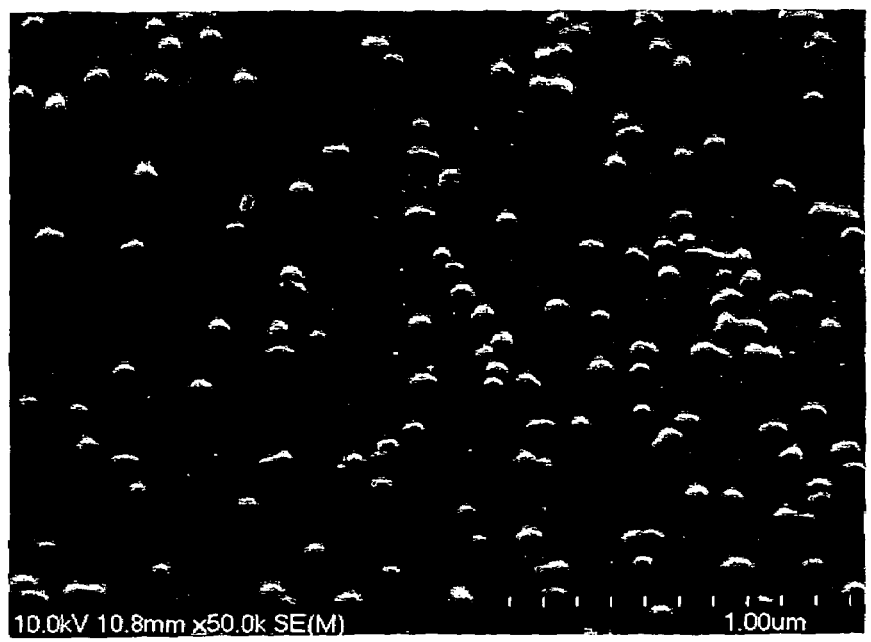
FIG. 5 is a scanning electron micrograph showing a surface of a copper film which has been planarized and cleaned with an organic acid solution.

In this cleaning process, an acid solution is preferably used for removing the damaged surface layer. In this case, it is desirable to use an organic acid such as citric acid, rather than an inorganic acid such as sulfuric acid. FIG. 4 shows a SEM (scanning electron microscope) image of a flattened surface that has been cleaned with an inorganic acid solution, and FIG. 5 shows a SEM image of a flattened surface that has been cleaned with an organic acid solution. As can be seen from FIGS. 4 and 5, the use of organic acid solution can achieve a smoother surface.

STEP 4 (Ellipsometry Measurement Step):

Ellipsometry is performed on the surface of the cleaned thin film so as to measure values of $\Delta$ (a phase angle of elliptically polarized light reflected from the surface) and $\Psi$ (a tangent given by a magnitude ratio of amplitude of the elliptically polarized light) of the copper film, which is not oxidized, to obtain $\Delta$s and $\Psi$s.

STEP 5 (Step of Determining an Optical Constant of the Copper Thin Film):

Based on $\Delta$s and $\Psi$s and the thickness d (reference thickness) of the copper thin film, an optical constant (refractive index) of the copper thin film is determined using a known method.

STEP 6 (Formation of an Oxide Film and Time-Series Ellipsometry Measurement):

The substrate is left at a room temperature so that an oxide film is formed on the surface of the copper film. At this time, ellipsometry is performed on the copper thin film having the oxide film with predetermined time intervals so as to measure a time-series variation in value of $\Delta$ and $\Psi$ of the oxide film for thereby obtaining $\Delta$f and $\Psi$f.

Figure 1:
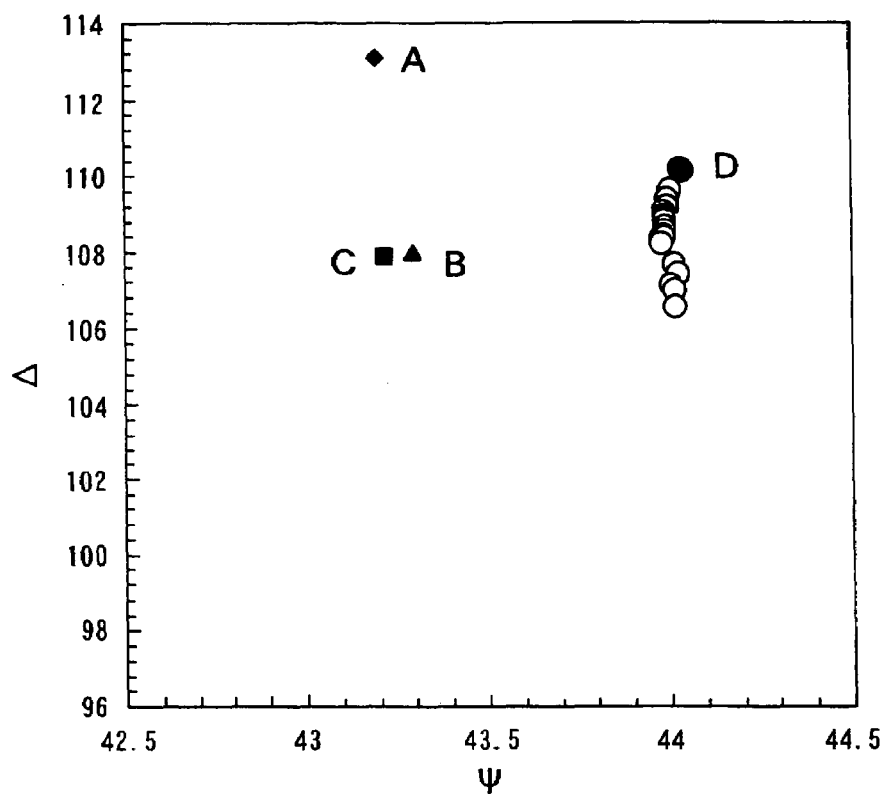
FIG. 1 is a graph of $\Delta$-$\Psi$ measured by ellipsometry, a sign D showing values ($\Delta$s, $\Psi$s) of $\Delta$ and $\Psi$ measured by ellipsometry performed on a clean surface of a copper thin film with no oxide film, and signs A, B, C showing values ($\Delta$f, $\Psi$f) of $\Delta$ and $\Psi$ obtained by calculation using three different known optical constants of copper.
Figure 2:
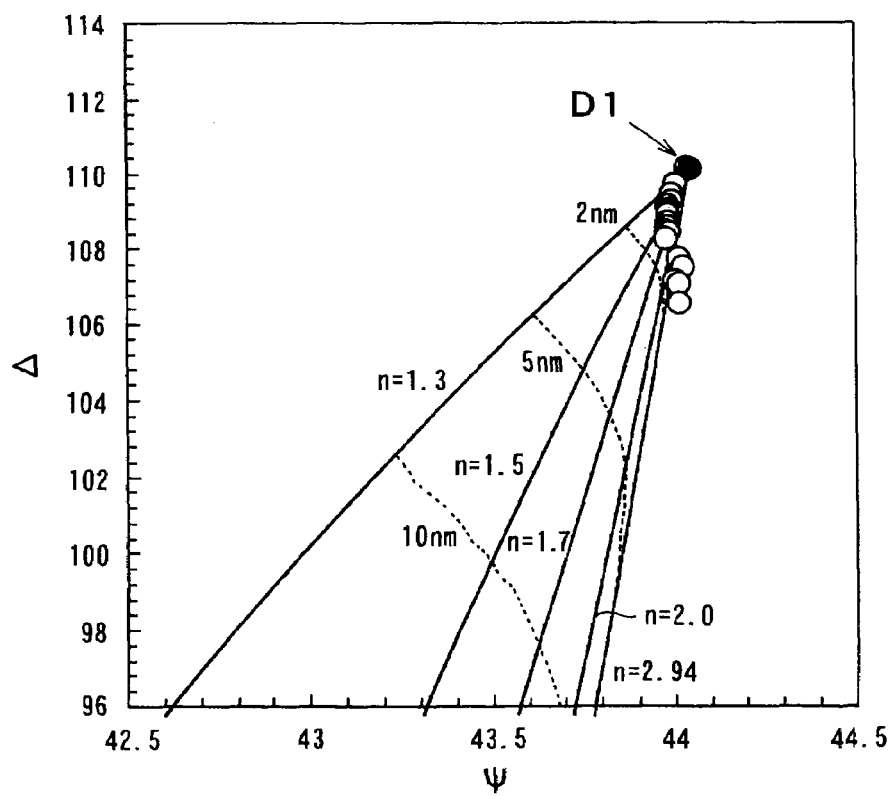
FIG. 2 is a graph showing a film thickness chart created using an optical constant as a parameter.

STEP 7 (Step of Preparing Chart of the Film Thickness):

As shown in FIG. 2, a $\Delta$-$\Psi$ graph is prepared. This $\Delta$-$\Psi$ graph is such that a region defined by vertical axis ($\Delta$) and horizontal axis ($\Psi$) covers $\Delta$s and $\Psi$s and peripheral values of $\Delta$s and $\Psi$s. D1, which represents the $\Delta$s and $\Psi$s that are measured when no oxide film is formed, is plotted in the graph, and then a film thickness chart is created with D1 ($\Delta$s, $\Psi$s) as a start point using an optical constant as a parameter. In the example shown in FIG. 2, a real number part n of the complex refractive index is used as the optical constant.

STEP 8 (Step of Determining the Film Thickness):

The time-series values ($\Delta$f, $\Psi$f), which were measured when the oxide film was formed, are plotted in the graph. From the plotted points and the above chart, it is possible to know a change in thickness of the oxidized copper film and to know an amount of increase in thickness, i.e., the thickness of the oxide film, and the optical constant.

STEP 9 (Step of Determining Film Thickness of other Substrate):

When an other substrate (i.e., a substrate to be subsequently polished) is removed from the cassette installed in the CMP apparatus and is to be polished, the thickness of the oxide film of this substrate is determined based on the time-series data on thickness of the oxide film which is obtained from STEP 8. Specifically, the thickness of the oxide film is determined from the elapsed time since the copper thin film was formed on this substrate.

STEP 10 (Planarization of the other Substrate):

Based on the film thickness determined by STEP 9, a planarization condition such as polishing time for the oxide film is determined, and the CMP process is then performed. For example, while the oxide film is pressed, a pressing force $P_1$ is set to be higher than a pressing force $P_2$ under which the copper film is pressed, and a pressing time under $P_1$ is determined according to the thickness of the oxide film. In a case where the film formation processes on the substrates in the cassette have been performed simultaneously under the same conditions, all of these substrates in the cassette are polished under the same planarization conditions.

With respect to the substrates having films formed under the same conditions, if the elapsed times since the formation of the films are different, the planarization times (polishing times) are set to be different. Specifically, the planarization condition for each of the substrates is determined from the time series data on the thickness of the oxide film obtained in STEP 8, and then the planarization is performed.

The above-mentioned substrate polishing method according to the embodiment of the present invention will be further described below with reference to the CMP apparatus illustrated in FIG. 6.

1. A substrate cassette 1 is loaded onto a load and unload station 2. The substrate is housed in the substrate cassette 1 in such a state that the copper film faces upwardly.

2. The substrate is removed from the substrate cassette 1 by a first transfer robot 4 and is then placed onto a temporary stage 7 or 8.

3. The substrate is transferred from the temporary stage to a reversing unit 31 by a second transfer robot 12 or a third transfer robot 13.

4. The substrate is reversed by the reversing unit 31 so that the copper film faces downwardly. The substrate is then delivered to a rotary transporter 32, and is transported to a pusher 36 by the rotary transporter 32.

5. The substrate held by the pusher 36 is attracted and held by a substrate carrier 26 under a vacuum pressure. Thereafter, the substrate is pressed against a polishing table 24 by the substrate carrier 26 and is thus polished.

6. When the eddy current film-thickness sensor or the optical film-thickness sensor (not shown) provided in the polishing table 24 detects that the copper film is polished to a predetermined thickness, the polishing of the substrate is stopped. The substrate is placed onto the pusher 36 and is then transported from the pusher 36 to the reversing unit 31 by the rotary transporter 32.

7. The substrate is reversed by the reversing unit 31 and is transferred to a cleaning module by the second transfer robot 12 or the third transfer robot 13. This cleaning module comprises cleaning units 5, 14 and 15 and a drying unit 6.

8. The substrate is cleaned and dried by the cleaning module.

9. After being dried, the substrate is transferred to an ex-situ ellipsometer 50 by the first transfer robot 4, so that the values of $\Delta$ and $\Psi$ of the copper film, i.e., $\Delta s$ and $\Psi s$, are measured by the ellipsometer 50.

10. After the film thickness is measured, the substrate is transferred to one of the temporary stages 7, 8, 9 and 10 by the first transfer robot 4.

11. After the substrate is left for a predetermined period of time, the substrate is transferred to the ellipsometer 50 by the first transfer robot 4, and then values ($\Delta f$, $\Psi f$) of $\Delta$ and $\Psi$ of an oxide film formed on the copper film of the substrate are measured by the ellipsometer 50.

12. Thereafter, the steps 10 and 11 are repeated, so that data on the thickness of the copper oxide film are obtained.

13. A polishing condition for an other substrate (i.e., a substrate to be subsequently polished) is set based on the data obtained by the steps 10-12, and the polishing of the other substrate is performed under this polishing condition.

Figure 6:
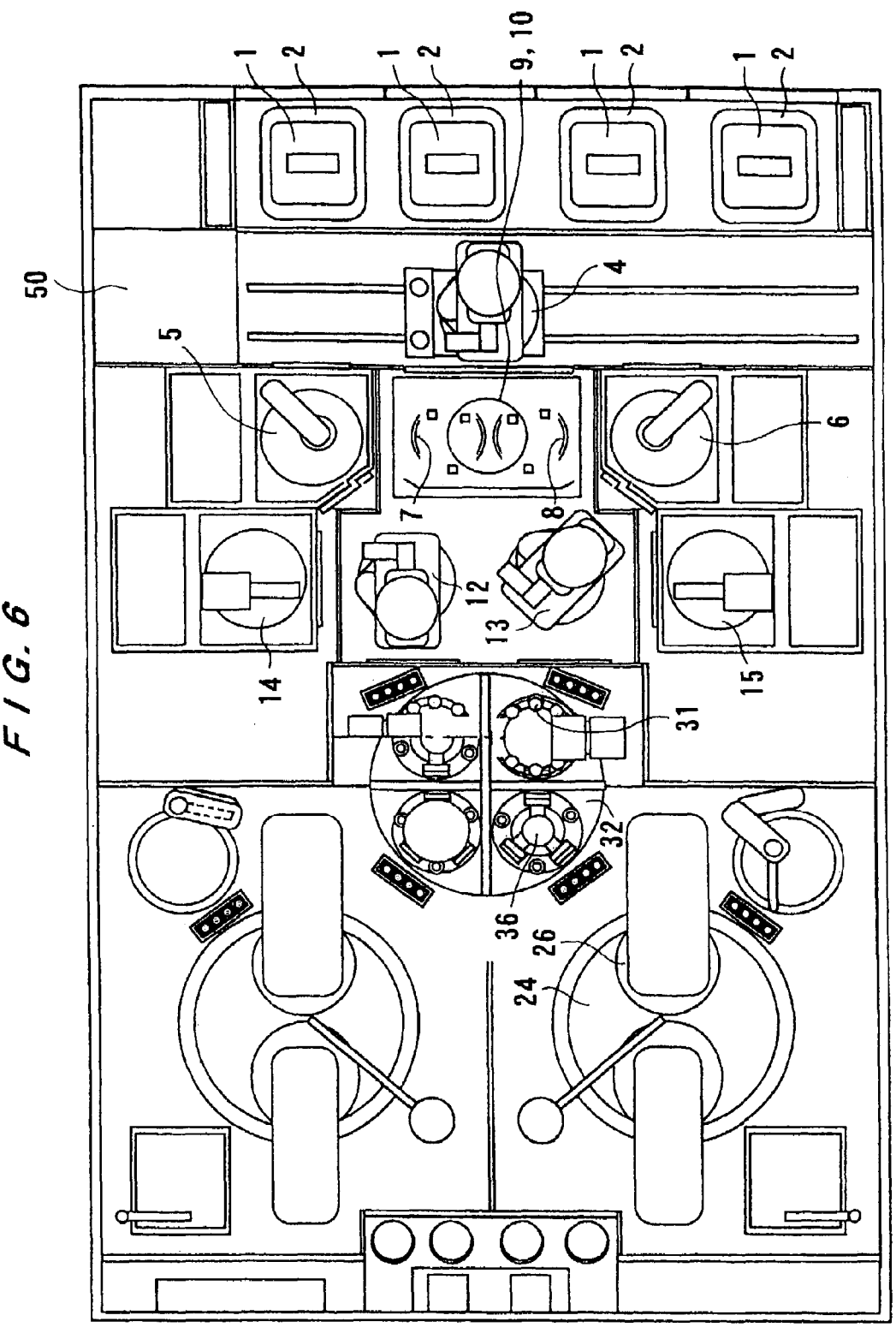
FIG. 6 is a plan view schematically showing a CMP apparatus for performing the polishing method according to an embodiment of the present invention.

In the CMP apparatus illustrated in FIG. 6, ellipsometry is performed outside the polishing table, i.e., performed in air after the surface to be measured is cleaned and dried. However, in consideration of efficiency, ellipsometry is preferably performed using an in-situ ellipsometer which is incorporated in the polishing table, i.e., performed in liquid.

Figure 7:
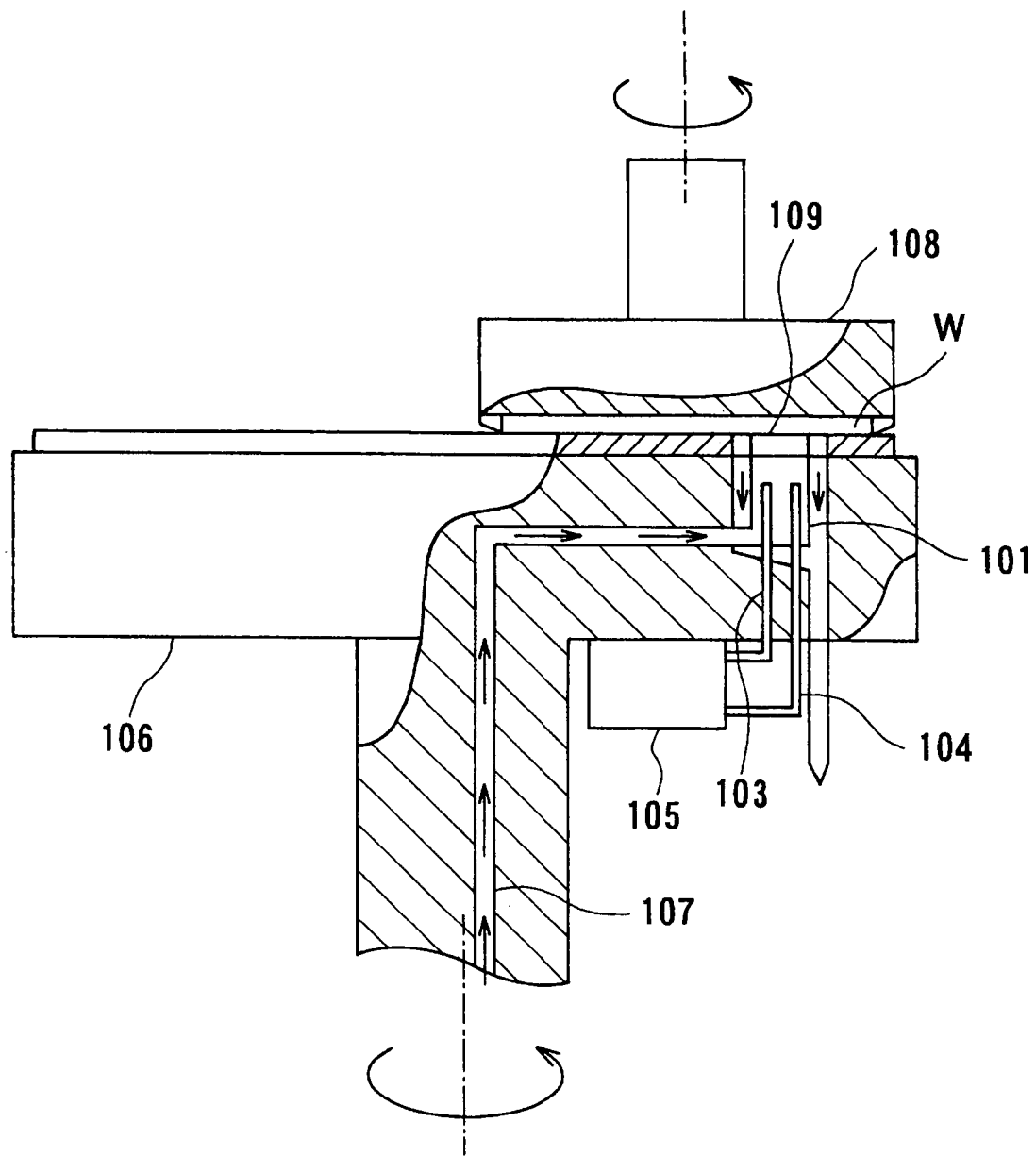
FIG. 7 is a cross-sectional side view showing a part of a CMP apparatus which incorporates an ellipsometer therein.

FIG. 7 shows an example of this type of ellipsometer. Specifically, FIG. 7 is a cross-sectional side view showing a part of a CMP apparatus which has an ellipsometer incorporated in a polishing table. As shown in FIG. 7, this CMP apparatus comprises a polishing table 106, and a substrate carrier 108 for holding a substrate W and pressing it against a polishing pad 109 on the polishing table 106.

The polishing table 106 has a fluid passage 107 for supplying water. A nozzle 101 is provided on an upper end portion of the fluid passage 107 and the water is ejected through the nozzle 101 toward the surface, to be polished, of the substrate W. The water that has been ejected to the surface of the substrate W flows downwardly along an outer circumferential wall of the nozzle 101 and is discharged to the exterior.

The ellipsometer comprises a light emitting fiber 103, a light receiving fiber 104, and a measuring unit 105. The light emitting fiber 103 and the light receiving fiber 104 are vertically movable so that a best Brewster angle in ellipsometry can be obtained.

While ellipsometry is being performed, the rotation of the substrate carrier 108 is stopped and, in order to keep a plane of incidence perpendicular to the substrate W, the pressing force of the substrate carrier 108 against the polishing pad 109 is kept constant. Further, in order to stabilize the optical path, the supply and discharge of the water may be stopped while ellipsometry is being performed. Alternatively, it is desirable to control the flow rate of the water so that laminar flow is formed.

Although a certain preferred embodiment of the present invention has been shown and described, it should be understood that the present invention is not limited to the above-mentioned embodiment. For example, the polishing method of the present invention can be applied to a metal film of Al, W, Ti, Ta and an insulating film. Ellipsometry to be used may be of a spectroscopic type or single wavelength type. However, since multiple layers are formed in the manufacturing of an IC chip, it is preferable to use spectroscopic ellipsometry.

What is claimed is:

1. A method of polishing a thin film on a substrate, said method comprising:
   planarizing a thin film on a reference substrate by performing a CMP process such that the thin film remains on the reference substrate as a planarized thin film;
   cleaning said planarized thin film, thereby providing a cleaned planarized thin film;
   measuring values of $\Delta$ and $\Psi$ with respect to said cleaned planarized thin film by performing ellipsometry; determining a physical property of said cleaned planarized thin film based on the values of $\Delta$ and $\Psi$ as measured;
   based on the physical property as determined, setting a polishing condition for another substrate having a thin film to be polished; and
   polishing said thin film of said another substrate in accordance with said polishing condition.

2. The method according to claim 1, wherein
   said thin film on said reference substrate has an oxide film on a surface thereof, such that planarizing said thin film results in removing said oxide film and providing an exposed surface of said thin film, and cleaning said planarized thin film comprises cleaning said exposed surface of said thin film so as to provide a cleaned exposed surface.

3. The method according to claim 2, further comprising:
   forming another oxide film on said cleaned exposed surface;
   measuring values of $\Delta$ and $\Psi$ with respect to said another oxide film by performing ellipsometry at predetermined time intervals; and
   determining a thickness of said another oxide film based on the values of $\Delta 0$ and $\Psi$ as measured with respect to said another oxide film,
   wherein setting a polishing condition for said another substrate includes determining a thickness of an oxide film on said thin film of said another substrate based on the thickness of said another oxide film as determined.

4. The method according to claim 3, wherein
   a thickness of said cleaned planarized thin film is set as a reference thickness, and determining a physical property of said cleaned planarized thin film based on the values of $\Delta$ and $\Psi$ as measured comprises determining a refractive index of said cleaned planarized thin film based on the values of $\Delta$ and $\Psi$ as measured and said reference thickness, and further comprising:
   calculating $\Delta$ and $\Psi$ corresponding to thicknesses and refractive indexes near said reference thickness and the refractive index as determined, respectively;
   determining a relationship between said thicknesses, said refractive indexes, and the $\Delta$ and $\Psi$ as calculated; and
   determining from said relationship thicknesses corresponding to the values of $\Delta$ and $\Psi$ with respect to said another oxide film as measured by performing said ellipsometry at the predetermined time intervals,
   wherein determining said thickness of said oxide film on said thin film of said another substrate comprises determining said thickness based on the thicknesses as determined from said relationship.

5. The method according to claim 4, wherein
   when film formation processes are performed on said reference substrate and said another substrate simultaneously under the same conditions, determining said thickness of said oxide film on said thin film of said another substrate comprises determining said thickness of said oxide film of said another substrate based on the thickness of said another oxide film as determined and a period of time from when said thin film is formed on said another substrate to when a CMP process is performed on said another substrate.

* * * * *